(12) United States Patent
Gelormini

(10) Patent No.: US 10,213,419 B2
(45) Date of Patent: Feb. 26, 2019

(54) COMPOUND IMPURITIES AND METHODS OF DETECTING SAME

(71) Applicant: AEGERION PHARMACEUTICALS, INC., Cambridge, MA (US)

(72) Inventor: Ann Gelormini, Cambridge, MA (US)

(73) Assignee: Aegerion Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 15/570,246

(22) PCT Filed: May 2, 2016

(86) PCT No.: PCT/US2016/030397
§ 371 (c)(1),
(2) Date: Oct. 27, 2017

(87) PCT Pub. No.: WO2016/176678
PCT Pub. Date: Nov. 3, 2016

(65) Prior Publication Data
US 2018/0133205 A1 May 17, 2018

Related U.S. Application Data

(60) Provisional application No. 62/154,906, filed on Apr. 30, 2015.

(30) Foreign Application Priority Data

Oct. 6, 2015 (BR) .......................... 1020150255020

(51) Int. Cl.
*A61K 31/4468* (2006.01)
*A61P 3/06* (2006.01)
*G01N 30/86* (2006.01)
*H01J 49/16* (2006.01)
*G01N 24/08* (2006.01)
*G01N 30/02* (2006.01)

(52) U.S. Cl.
CPC ............ *A61K 31/4468* (2013.01); *A61P 3/06* (2018.01); *G01N 30/8675* (2013.01); *H01J 49/164* (2013.01); *G01N 24/087* (2013.01); *G01N 2030/027* (2013.01)

(58) Field of Classification Search
CPC .............. A61K 31/4468; A61K 31/192; A61K 39/3955; C07K 16/40; C12N 2310/11; C12N 2320/31
USPC .......................................... 546/224; 514/329
See application file for complete search history.

(56) References Cited

U.S. PATENT DOCUMENTS 5,712,279 A * 1/1998 Biller .................... C07D 211/58
514/228.8
6,288,234 B1 * 9/2001 Griffin .................... A61K 31/00
546/190

FOREIGN PATENT DOCUMENTS

WO WO 2006/127932 A2 * 11/2006

OTHER PUBLICATIONS

PubChem CID 57148250 (2012).*

* cited by examiner

*Primary Examiner* — Deepak R Rao
(74) *Attorney, Agent, or Firm* — Haug Partners LLP

(57) ABSTRACT

The present disclosure relates to compositions comprising impurities (e.g., carbamate and/or hydrolysis products) in a lomitapide sample and methods of detecting such impurities.

16 Claims, No Drawings

COMPOUND IMPURITIES AND METHODS OF DETECTING SAME

CROSS-REFERENCE TO RELATED APPLICATIONS

This application is filed pursuant to 35 U.S.C. § 371 based on International Application No. PCT/US2016/030397, filed May 2, 2016, which claims priority to U.S. Provisional Application No. 62/154,906 filed Apr. 30, 2015 and Brazilian Patent Application No. BR1020150255020 filed Oct. 6, 2015, both of which are hereby incorporated by reference.

BACKGROUND

Lomitapide is a microsomal triglyceride transfer protein (MTP) inhibitor shown clinically to lower plasma cholesterol levels. Lomitapide, also known as N-(2,2,2-Trifluoroethyl)-9-[4-[4-[[[4'-(trifluoromethyl)[1,1'biphenyl]-2-Y1]carbonyl]amino]-1-piperidinyl]butyl]9H-fluorene-9-carboxamide, is approved to treat homozygous familial hypercholesterolemia (HoFH), a serious genetic disorder which, if left untreated, leads to the development of atherosclerosis.

However, lomitapide (e.g., a lomitapide mesylate salt) can contain process impurities, including unreacted starting materials, chemical derivatives of impurities contained in starting materials, synthetic by-products, and degradation products. Such impurities present in a lomitapide composition can arise, e.g., from degradation, including during storage or during the manufacturing process, including the chemical synthesis.

In addition to stability, which may be a factor in the shelf life of lomitapide, the purity of lomitapide produced in the commercial manufacturing process is an important condition for commercialization. Impurities introduced during commercial manufacturing processes must be limited to small amounts, and are preferably substantially absent.

At certain stages during processing of lomitapide, it can be analyzed for purity, e.g., by high performance liquid chromatography (HPLC) or thin layer chromatography (TLC), to determine if it is suitable for continued processing and, ultimately, for use in a pharmaceutical product. In the United States, the Food and Drug Administration guidelines recommend that the amounts of some impurities be limited to less than, for example, 0.1 percent.

Therefore, a continuing need exists to identify potential lomitapide impurities and to develop readily usable identification methods to determine the presence and/or quantity of a lomitapide impurity in a lomitapide composition.

SUMMARY

The present disclosure provides, in part, compositions of lomitapide and/or methods for detecting impurities in a lomitapide composition.

In one aspect, the disclosure provides a lomitapide composition including lomitapide or a pharmaceutically acceptable salt thereof and a compound represented by

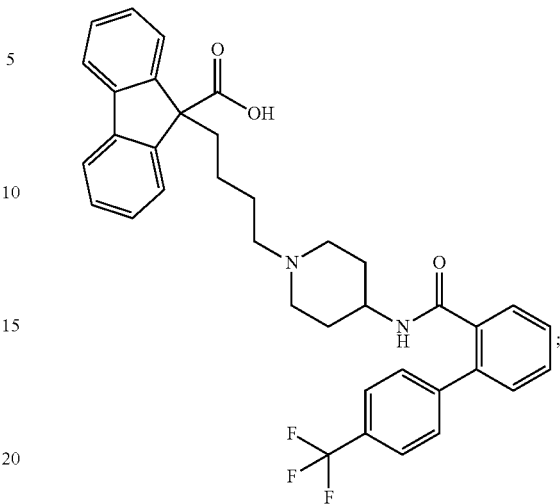

and a pharmaceutically acceptable excipient.

In another aspect, the disclosure provides a lomitapide composition including lomitapide or a pharmaceutically acceptable salt thereof, and a carbamate product represented by

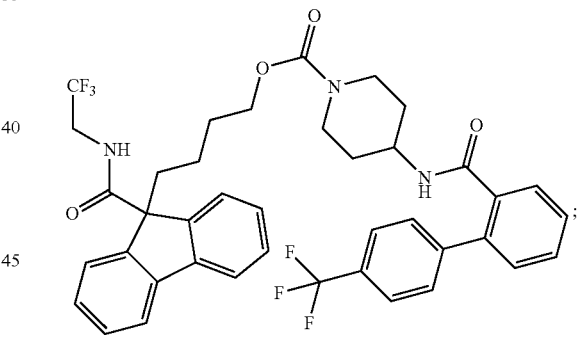

and a pharmaceutically acceptable excipient.

In certain embodiments, a disclosed lomitapide composition has less than about 0.5 weight percent of an impurity (e.g., an identified hydrolysis product or carbamate product). In certain embodiments, after storage at 25° C. for 12 months, a disclosed lomitapide composition comprises less than about 0.1% of an identified impurity (e.g., hydrolysis product or carbamate product).

In another aspect, the disclosure relates to tablets containing a lomitapide composition as described herein.

In another aspect, the disclosure relates to a composition having the following structure:

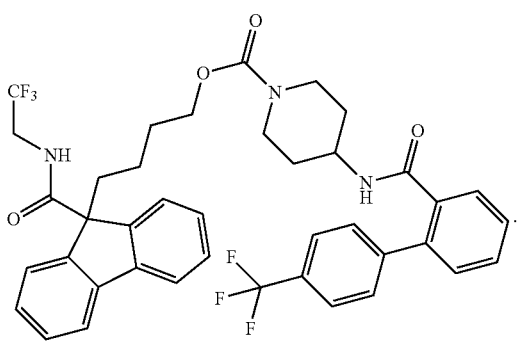 [SMILES: O=C(NC1CCN(C(=O)OCCCCC2(C(=O)NCC(F)(F)F)c3ccccc3-c3ccccc32)CC1)c1ccccc1-c1ccc(C(F)(F)F)cc1]

In another aspect, the disclosure provides a method for analyzing a lomitapide composition sample for the presence or amount of an impurity. The method includes providing a lomitapide composition sample; using a spectral or toxicology analysis to determine the presence of a compound selected from:

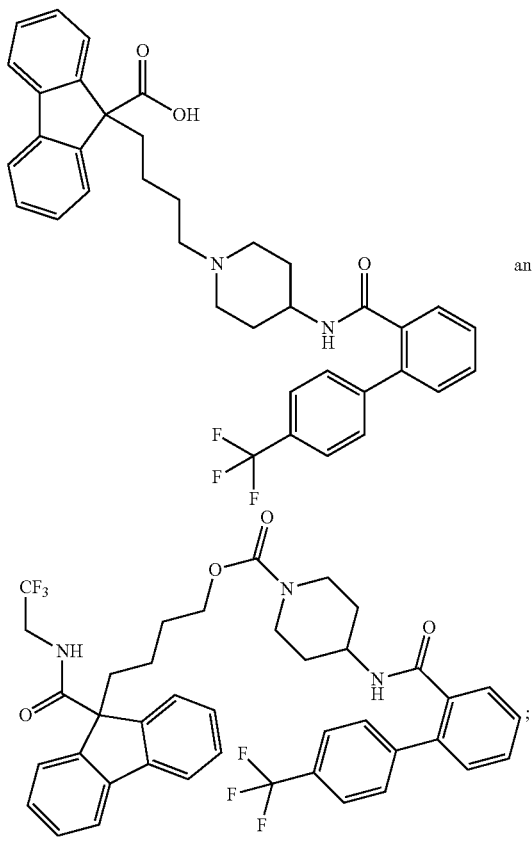

making a determination about the lomitapide composition sample based on a comparison of the structural or toxicological signal associated with the compound to a reference standard for lomitapide or a pharmaceutically acceptable salt thereof; and determining the presence of the structural or toxicological signature associated with the compound thereby to analyze the lomitapide composition sample.

In certain embodiments, the level of a structural signature is calculated as the area under the curve or as the percent relative amount of each fraction present in the lomitapide composition sample. Such structural signatures can be determined using, e.g., HPLC optionally coupled with mass spectrometry (MS), nuclear magnetic resonance (NMR) spectroscopy, matrix-assisted laser desorption/ionization mass spectroscopy (MALDI-MS), a fluorometric assay, an enzyme-linked immunosorbent assay (ELISA), a chromatogenic assay, and a colorimetric assay.

In another aspect, the disclosure provides a method for analyzing a lomitapide composition sample for the presence or amount of an impurity. The method includes providing a lomitapide composition sample, using a spectral method to determine the presence of a compound selected from

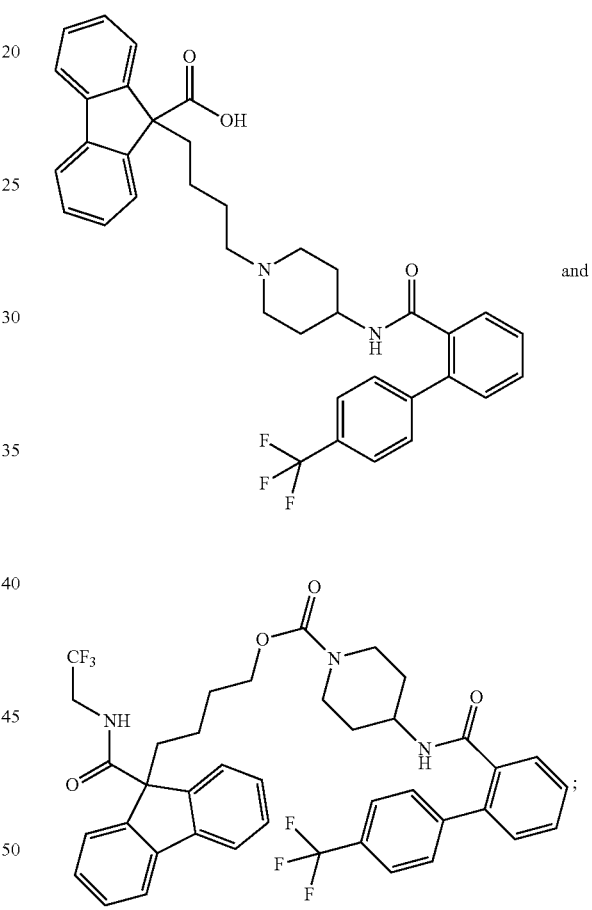

making a determination about the lomitapide composition sample based on a comparison of the molecular weight associated with the compound to a reference standard for lomitapide or a pharmaceutically acceptable salt thereof; and determining the molecular weight associated with the compound thereby to analyze the lomitapide composition sample.

In another aspect, the disclosure provides a method for determining an amount of an impurity in a composition sample comprising lomitapide or a pharmaceutically acceptable salt thereof, e.g., a mesylate salt, the method comprising determining an amount of a compound selected from

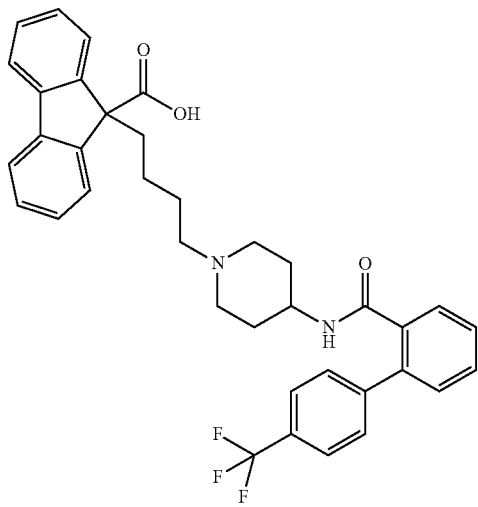

in the sample; and correlating the amount the compound in the sample with the amount of lomitapide in the sample.

DETAILED DESCRIPTION

Lomitapide can be unstable and prone to produce impurities upon manufacture, including, e.g., a carbamate impurity, and/or storage, including, e.g., a hydrolysis impurity. The disclosure relates in part to compositions and methods for analyzing a lomitapide sample for the presence or amount of an impurity (e.g., a degradation product of lomitapide). Degradation products may be isolated using chromatography or other methods described herein.

I. Compositions

As described herein, the disclosure relates to a lomitapide composition including lomitapide or a pharmaceutically acceptable salt thereof and a composition represented by

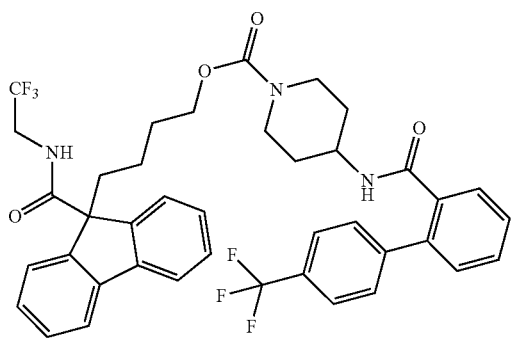

or

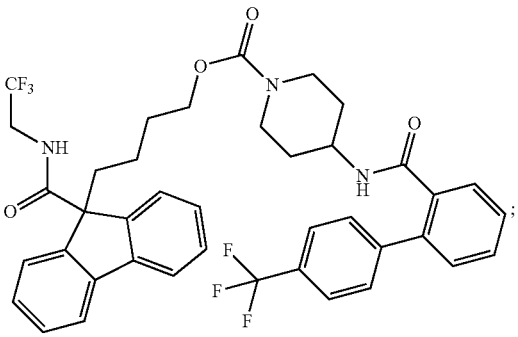 [SMILES: O=C(NC1CCN(C(=O)OCCCCC2(C(=O)NCC(F)(F)F)c3ccccc3-c3ccccc32)CC1)c1ccccc1-c1ccc(C(F)(F)F)cc1]

and a pharmaceutically acceptable excipient.

The disclosure also relates to a lomitapide composition comprising lomitapide or a pharmaceutically acceptable salt thereof, and a carbamate product represented by and a pharmaceutically acceptable excipient. Such a carbamate product may be an impurity in certain lomitapide compositions such as compositions prepared by certain synthetic routes.

Disclosed lomitapide compositions can have less than about 0.5 weight percent of an identified impurity (e.g., a hydrolysis product or carbamate product), less than about 0.4 weight percent of the impurity, less than about 0.3 weight percent of the impurity, less than about 0.2 weight percent of the impurity, less than about 0.1 weight percent of the impurity, or less than about 0.01 weight percent of the impurity. For example, a disclosed lomitapide composition can have between about 0 and about 1 weight percent of an impurity; between about 0.0001 and about 1 weight percent of an impurity; between about 0.0001 and about 0.1 weight percent of an impurity; between about 0.0001 and about 0.01 weight percent of an impurity; between about 0.0001 and 0.001 weight percent of an impurity; between about 0.001 and about 1 weight percent of an impurity; between about 0.001 and about 0.1 weight percent of an impurity; between about 0.001 and about 0.01 weight percent of an impurity; between about 0.01 and about 1 weight percent of an impurity; between about 0.01 and about 0.1 weight percent of an impurity. In certain embodiments, a disclosed lomitapide composition can have between about 0 and about 0.2 weight percent of an impurity; between about 0 and about 0.5 weight percent of an impurity; between about 0 and about 1 weight percent of an impurity; between about 0 and about 2 weight percent of an impurity; between about 0 and about 5 weight percent of an impurity; between about 0.1 and about 0.2 weight percent of an impurity; between about 0.1 and about 0.5 weight percent of an impurity; between about 0.1 and about 2 weight percent of an impurity; between about 0.1 and about 5 weight percent of an impurity; between about 0.2 and about 0.5 weight percent of an impurity; between about 0.2 and about 1 weight percent of an impurity; between about 0.2 and about 2 weight percent of an impurity; between about 0.2 and about 5 weight percent of an impurity; between about 0.5 and about 1 weight percent of an impurity; between about 0.5 and about 2 weight percent of an impurity; and between about 0.5 and about 5 weight percent of an impurity.

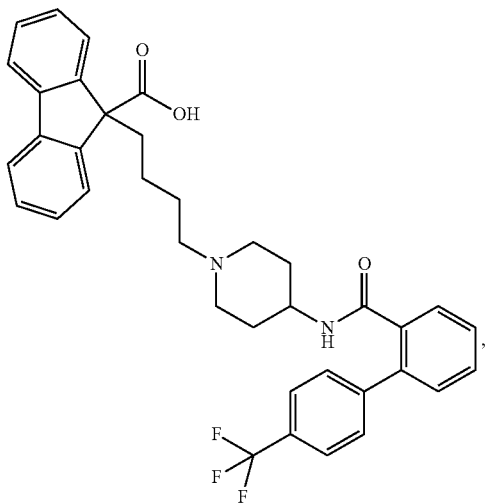 [SMILES: O=C(NC1CCN(CCCCC2(C(=O)O)c3ccccc3-c3ccccc32)CC1)c1ccccc1-c1ccc(C(F)(F)F)cc1]

For example, a hydrolysis product/impurity may be represented by and a carbamate product/impurity may be represented by

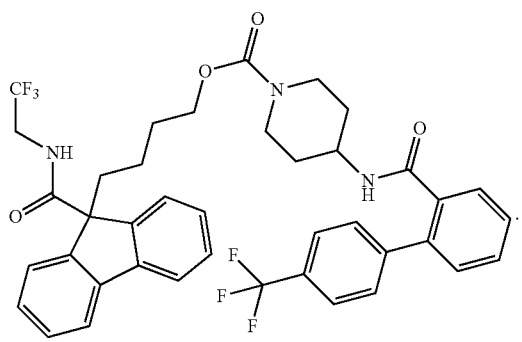 [SMILES: O=C(NC1CCN(C(=O)OCCCCC2(C(=O)NCC(F)(F)F)c3ccccc3-c3ccccc32)CC1)c1ccccc1-c1ccc(C(F)(F)F)cc1]

In certain embodiments, after storage at about 5° C., at about 25° C., or at about 40° C. for less than or about 36 months, 24 months, 12 months, 6 months, 5 months, 4 months, 3 months, 2 months, or 1 month, a lomitapide composition can comprise less than about 1%, less than about 0.5%, less than about 0.1%, less than about 0.05%, less than about 0.01%, less than about 0.005%, or less than about 0.001% of an impurity (e.g., a hydrolysis product). In certain embodiments, storage conditions are about 40° C./75% relative humidity (RH) for about 4 months or about 6 months or about 25° C./60% RH for about 12 months, about 24 months, or about 36 months.

In another aspect, the disclosure provides tablets containing a lomitapide composition as described herein. A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. The disclosed excipients may serve more than one function. For example, fillers or binders may also be disintegrants, glidants, anti-adherents, lubricants, sweeteners and the like.

The disclosure further relates to a composition having the following structure:

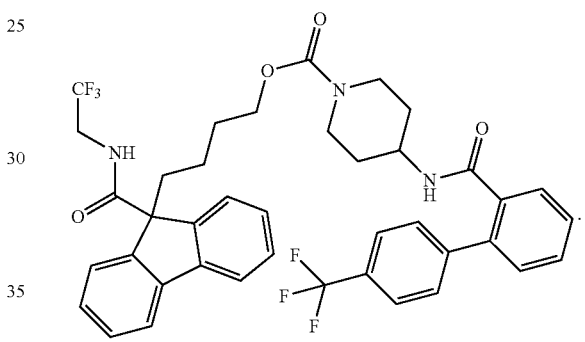

II. Methods

As disclosed herein, the disclosure also relates to a method for analyzing a lomitapide composition sample for the presence or amount of an impurity. The method includes providing a lomitapide composition sample; using a spectral or toxicology method to determine the presence of a compound selected from:

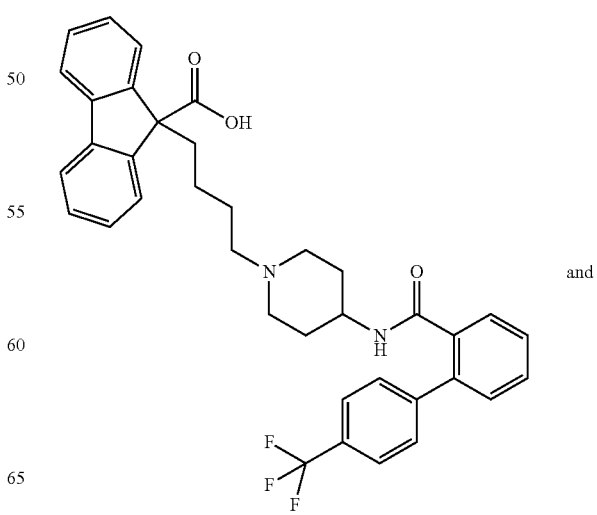

and

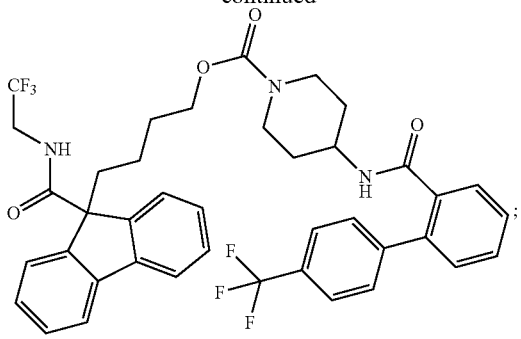

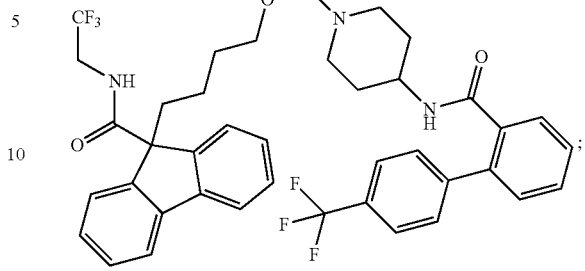

making a determination about the lomitapide composition sample based on a comparison of the structural or toxicological signal associated with the compound to a reference standard for lomitapide or a pharmaceutically acceptable salt thereof; and determining the presence of the structural or toxicological signature associated with the compound thereby to analyze the lomitapide composition sample.

In certain embodiments, the level of the structural or toxicological signature is calculated as the area under the curve or as the percent relative amount of each fraction present in the lomitapide composition sample. The structural or toxicological signature can be determined using an assay known in the art, including, e.g., HPLC optionally coupled with mass spectrometry (MS), nuclear magnetic resonance (NMR) spectroscopy, matrix-assisted laser desorption/ionization mass spectroscopy (MALDI-MS), a fluorometric assay, an enzyme-linked immunosorbent assay (ELISA), a chromatogenic assay, and a colorimetric assay. For example, the structural or toxicological signature can be identified using HPLC-MS/NMR. In certain embodiments, the structural or toxicological signature is identified using a combined HPLC and MS analysis, such as API-300 Sciex, HPLC PerkinElmer 200, Autosampler PerkinElmer 200. The MS can be performed by using triple-Q HPLC/MS analysis.

In another aspect, the disclosure provides a method for analyzing a lomitapide composition sample for the presence or amount of an impurity. The method includes providing a lomitapide composition sample, using a spectral method to determine the presence of a compound selected from

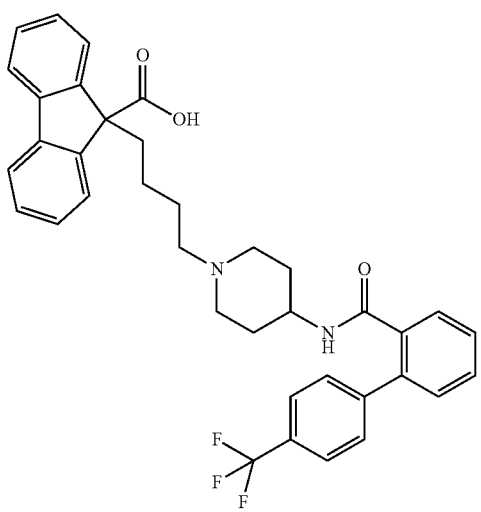

and making a determination about the lomitapide composition sample based on a comparison of the molecular weight associated with the compound to a reference standard for lomitapide or a pharmaceutically acceptable salt thereof; and determining the molecular weight associated with the compound thereby to analyze the lomitapide composition sample.

A method for determining an amount of an impurity in a composition sample comprising lomitapide or a pharmaceutically acceptable salt thereof, the method comprising determining an amount of a compound selected from

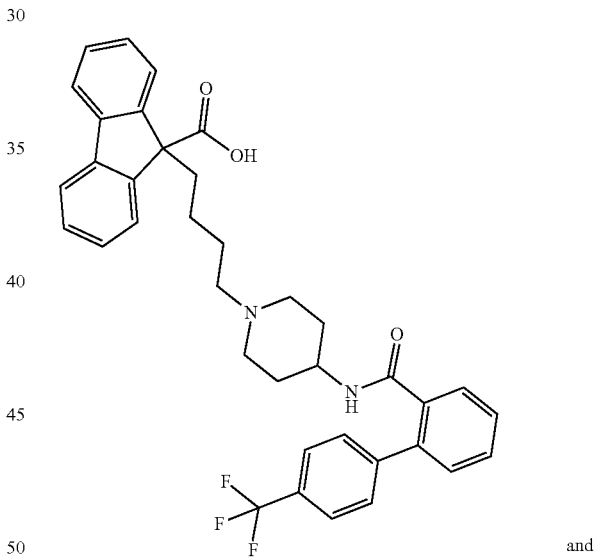

and

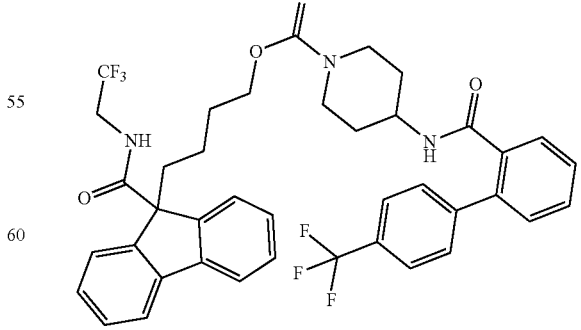

in the sample; and correlating the amount the compound in the sample with the amount of lomitapide in the sample.

EXAMPLES

Example 1: Synthetic Route

In a 1 L jacketed reactor was combined 1 (20.01 g), 2 (24.40 g), K$_2$CO$_3$ (20.05 g), and DMF (244 mL), as depicted in the above scheme. Vacuum was applied with stirring in the vessel and was held for 2 minutes. The vessel was released to nitrogen and the vacuum/nitrogen purging was completed twice more in a similar fashion. The mixture was held with stirring at 65° C. for 7.5 h, then cooled to 45° C. overnight. The carbamate impurity was 2.5% by HPLC. The reaction mixture was cooled to 21° C. The solids were removed by filtration and washed with MTBE (165 mL). The DMF/MTBE mixture was transferred back to the 1 L reactor and DI water was charged (192 mL). The mixture was stirred for 10 minutes and the layers were allowed to separate. The aqueous layer was extracted with MTBE (154 mL) for 10 minutes and the layers were allowed to separate. The aqueous layer was discarded. The organic layers were combined, washed with DI water (80 mL) for 10 minutes, and the layers were allowed to separate. The remaining organic layer was washed with DI water (50 mL) for 10 minutes and the layers were allowed to separate. The organic layer was concentrated to a residue on a rotary evaporator (bath temp: 50° C.). Ethanol (SDA-3C, 50 mL) was added and the reaction mixture was concentrated to a residue on a rotary evaporator (bath temp: 50° C.). Ethanol (SDA-3C, 50 mL) was added and the reaction mixture was concentrated to a residue on a rotary evaporator (bath temp 50° C.). Ethanol (SDA-3C, 50 mL) was added and the total volume was approximately 65 mL. The reaction mixture was heated to 75° C., resulting in a clear solution. n-Heptane (295 mL, heated to 75° C.) was added to the reaction mixture while maintaining an internal temperature of 70-75° C. The reaction mixture was cooled to 25° C. over 2.5 hours and was then stirred overnight at ambient temperature. The solids were removed by filtration. The filtrate (approximately 12% carbamate) was concentrated to a residue (approximately 3.5 g). The carbamate was isolated by column chromatography (SiO$_2$/DCM, eluting with 1:1 ethyl acetate/heptane) to afford approximately 100 carbamate. Full NMR structural confirmation was performed by (see Example 2) and the results are consistent with a carbamate of lomitapide. LC/MS: Calc'd for M+H=738.3, found m/z 738.3 (AJS-ES pos). Calc'd for M−H=736.3, found m/z 736.2 (AJS-ES neg).

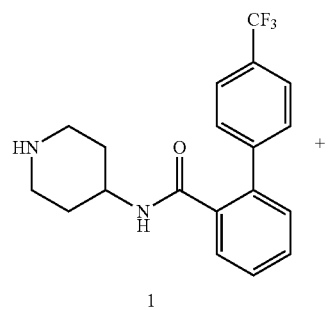

1

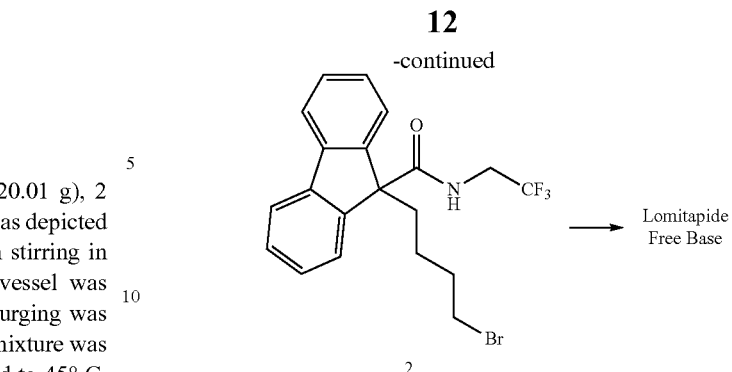

2

→ Lomitapide Free Base

Example 2: Identification of a Carbamate

Identification of a carbamate impurity of lomitapide was confirmed using NMR spectroscopy. 32.5 mg of a suspected impurity was weighed out and dissolved in about 0.75 mL CDCl$_3$ containing TMS. $^1$H, $^{13}$C, DEPT-135, COSY, HSQC, and HMBC spectra, followed by a second $^1$H spectrum, were acquired at ambient temperature on a Varian Inova NMR spectrometer operating at 500 MHz for $^1$H and 126 MHz for $^{13}$C.

The resulting FIDs were transferred to a PC and processed using NUTS NMR processing software from Acorn NMR Inc. (Livermore, Calif.). $^1$H chemical shifts were referenced to TMS, 0 ppm. Per IUPAC recommendations for referencing of NMR spectra (Harris et al. (2001) PURE AND APPLIED CHEMISTRY, 73:1795-1818), the $^{13}$C chemical shifts were referenced using the "unified scale" to the absolute $^1$H frequency of 0 ppm.

Based on the NMR spectra, the structure of the carbamate impurity was confirmed as:

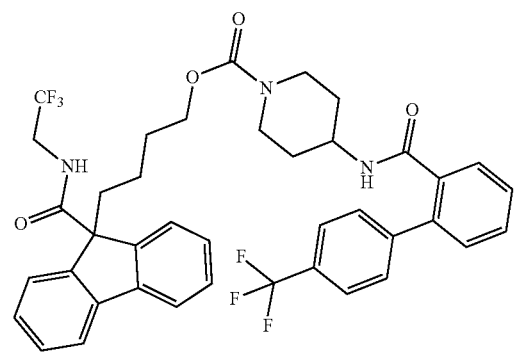

$^1$H and $^{13}$C chemical shifts are listed in Table 1.

TABLE 1

| Label | δ $^{13}$C (ppm) | δ $^1$H (ppm) | Multiplicity, splitting (Hz) (a) |
|---|---|---|---|
| 4 | 173.3 | — | — |
| 20 | 168.4 | — | — |
| 32 | 155.2 | — | — |
| 6 | 145.0 | — | — |
| 27 | 144.0 | — | — |
| 11 | 141.0 | — | — |
| 26 | 138.1 | — | — |
| 21 | 136.1 | — | — |
| 24 | 130.3 | 7.50 | dd, 7.6, 7.6, 1.5 |
| 30 | 130.0, 33 Hz | — | — |

TABLE 1-continued

| Label | δ $^{13}$C (ppm) | δ $^1$H (ppm) | Multiplicity, splitting (Hz) (a) |
|---|---|---|---|
| 25 | 130.1 | 7.36 (b) | overlapping |
| 28 | 129.1 | 7.53 | m |
| 9 | 128.6 | 7.43 | ddd, 7.6, 7.6, 1.0 |
| 22 | 128.4 or 128.3 | 7.64 | dd, 7.7, 1.5 |
| 23 | 128.3 or 128.4 | 7.45 | ddd, 7.6, 7.6, 1.2 |
| 8 | 128.1 | 7.35 (b) | overlapping |
| 29 | 125.4, 4 Hz | 7.67 | m |
| 31 | 124.1, 272 Hz | — | — |
| 7 | 124.2 | 7.52 | d, 7.3 |
| 1 | 123.8, 279 Hz | — | — |
| 10 | 120.5 | 7.75 | d, 7.6 |
| 15 | 64.9 | 3.83 | t, 6.4 |
| 5 | 62.4 | — | — |
| 18 | 46.7 | 3.89 | m |
| 16 | 42.4 | 2.73 | m |
|  |  | 3.58-3.89 (b) | m |
| 2 | 40.6, 34 Hz | 3.62 | dq, 6.8, 9.0 |
| 12 | 35.8 | 2.42 | m |
| 17 | 31.3 | 1.59, 0.94 | m |
| 14 | 28.8 | 1.43 | m |
| 13 | 20.2 | 0.72 | m |
| 3 | — | 5.36 | t, 6.3 |
| 19 | — | 5.31 | d, 8.4 |

(a) s = singlet, d = doublet, t = triplet, q = quartet, m = multiplet
(b) Chemical shift obtained from HSQC spectrum HMBC correlations are listed in Table 2.

TABLE 2

| $^1$H ------------------------------> $^{13}$C | |
|---|---|
| 2 | 1, 4 |
| 3 | 2, 4 |
| 7 | 5, 9, 10, 11 |
| 8 | 6, 7, 10, 11 |
| 9 | 6, 7, 10, 11 |
| 10 | 6, 7, 8, 11 |
| 12 | 4, 5, 6, 13, 14 |
| 13 | 5, 12, 14, 15 |
| 14 | 12, 13, 15 |
| 15 | 13, 14, 32 |
| 19 | 17, 18, 20 |
| 22 | 20, 24, 26 |
| 23 | 21, 25, 26 |
| 24 | 22, 26 |
| 25 | 21, 23, 27 |
| 28 | 26, 29, 30 |
| 29 | 27, 28, 29 (symmetry), 31 |

For any protonated carbon, assignment of either the proton or the carbon can be used to assign the other using the HSQC spectrum. In addition, protonated carbons having odd multiplicity (methyls and methines) may be distinguished from carbons having even multiplicity (methylenes) using the DEPT-135 spectrum. Quaternary carbons are identified by comparison of the $^{13}$C with the DEPT and/or HSQC spectra, as only protonated carbons are observed in either the DEPT or HSQC. Geminal methylene protons are identified from the HSQC spectrum as 2 protons with correlations to the same carbon. Protons on N are identified by absence of HSQC correlations.

$^{13}$C assignments were made based on chemical shift, multiplicity, and C—F coupling. $^1$H assignments were made based on chemical shift, integration, and coupling pattern.

The NMR data are consistent with the proposed structure above. A few unidentified impurity peaks were also observed.

Example 3: Synthesis

The following synthetic scheme can be used to prepare the following compound which would allow identification or presence in, e.g., a sample of lomitapide.

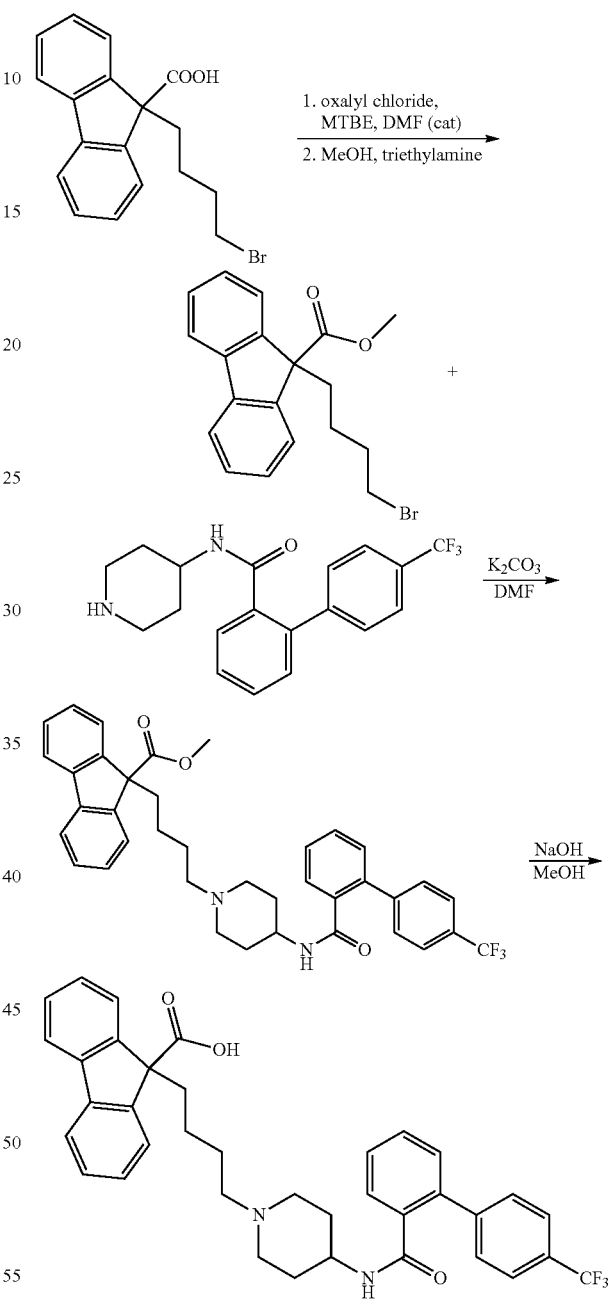

Example 4: Identification of a Hydrolysis Product

During stability testing of lomitapide, an impurity with an RRT of 0.85 was observed to be increasing in stability samples stored at 40° C./75% RH at 4 and 6 months and stored at 25° C./60% RH at 12, 24, and 36 months. A study was performed to identify this impurity using LC/MS/MS. Based on the fragmentation patterns of both lomitapide and the impurity at RRT 0.85, the structure of the impurity at RRT 0.85 has been identified to be a degradation product of lomitapide due to hydrolysis having the structure:

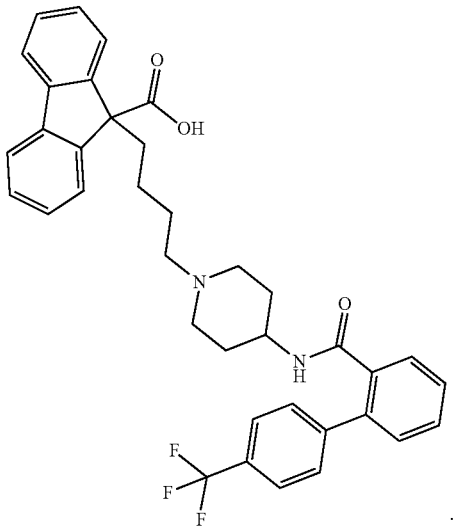 [SMILES: O=C(NC1CCN(CCCCC2(C(=O)O)c3ccccc3-c3ccccc32)CC1)c1ccccc1-c1ccc(C(F)(F)F)cc1]

EMBODIMENTS

1. A lomitapide composition comprising: lomitapide or a pharmaceutically acceptable salt thereof, and a second compound represented by:

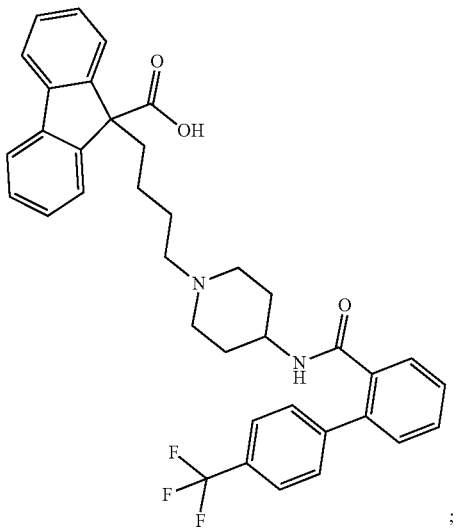 [SMILES: O=C(NC1CCN(CCCCC2(C(=O)O)c3ccccc3-c3ccccc32)CC1)c1ccccc1-c1ccc(C(F)(F)F)cc1]

and a pharmaceutically acceptable excipient.
2. The therapeutic composition of embodiment 1, wherein the lomitapide composition has less than about 0.5 weight percent of the second compound.
3. The therapeutic composition of embodiment 1 or 2, wherein after storage at about 25° C. for about 12 months, the composition comprises less than about 0.1% of the second compound.
4. A tablet comprising the lomitapide composition of any one of embodiments 1-3.
5. A lomitapide composition comprising: lomitapide or a pharmaceutically acceptable salt thereof, and a carbamate product represented by

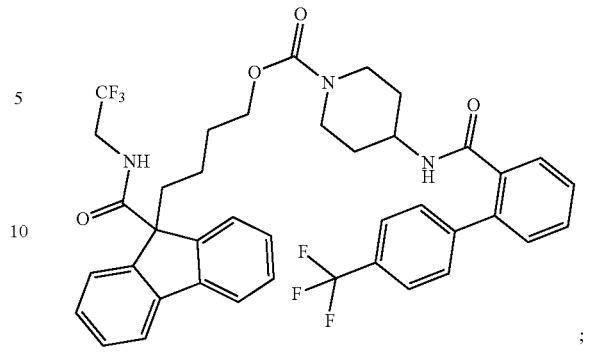

and
a pharmaceutically acceptable excipient.
6. A tablet comprising the lomitapide composition of embodiment 5.
7. A lomitapide product having the following structure:

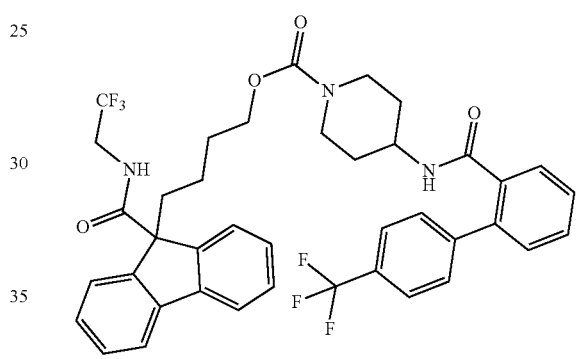

8. A method for analyzing a lomitapide composition sample for the presence or amount of an impurity comprising:
providing a lomitapide composition sample;
using a spectral or toxicology analysis to determine the presence of a compound selected from:

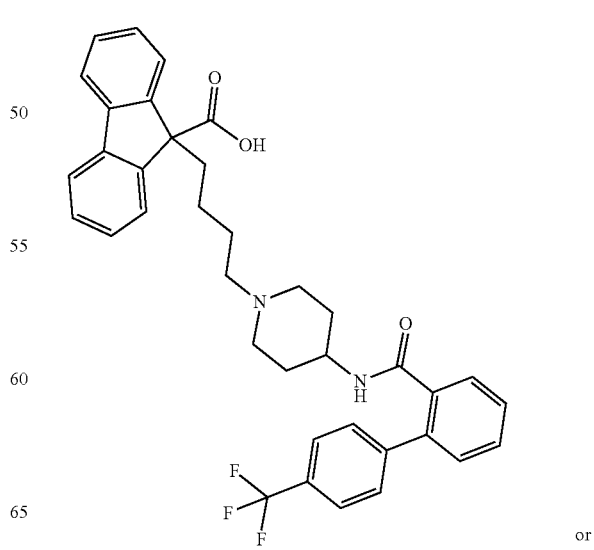

or

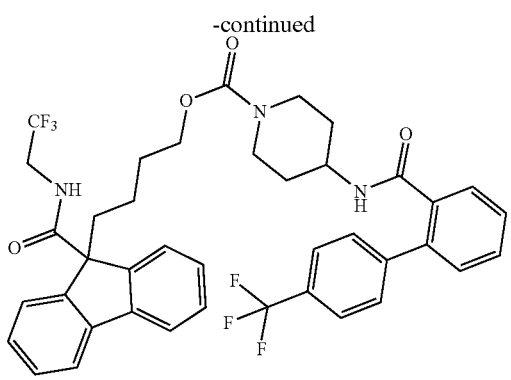

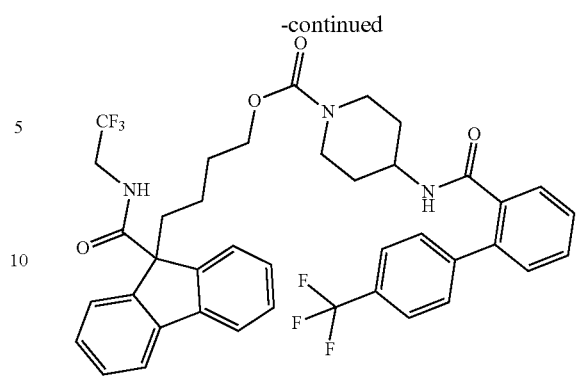

making a determination about the lomitapide composition sample based on a comparison of a structural signal associated with the compound to a reference standard for lomitapide or a pharmaceutically acceptable salt thereof; and determining the presence of the structural signature associated with the compound thereby to analyze the lomitapide composition sample.

9. The method of embodiment 8, wherein a level of the structural signature is calculated as the area under the curve or as the percent relative amount of each fraction present in the lomitapide composition sample.

10. The method of embodiment 9, wherein the structural signature is determined using high performance liquid chromatography (HPLC).

11. The method of embodiment 9, wherein the structural signature is determined using nuclear magnetic resonance (NMR) spectroscopy.

12. The method of embodiment 9, wherein the structural signature is determined using matrix-assisted laser desorption/ionization mass spectroscopy (MALDI-MS).

13. The method of embodiment 9, wherein the structural signature is determined using one or more of a fluorometric assay, an enzyme-linked immunosorbent assay (ELISA), a chromatogenic assay, and a colorimetric assay.

14. A method for analyzing a lomitapide composition sample for the presence or amount of an impurity comprising:

providing a lomitapide composition sample;

using a spectral analysis to determine the presence of a compound selected from:

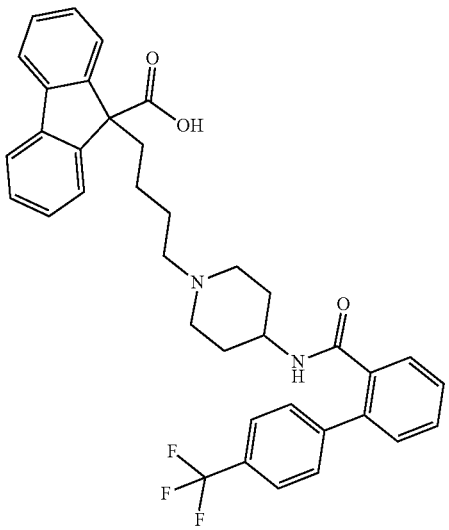

or making a determination about the lomitapide composition sample based on a comparison of the molecular weight associated with the compound to a reference standard for lomitapide or a pharmaceutically acceptable salt thereof; and determining the molecular weight associated with the compound thereby to analyze the lomitapide composition sample.

15. A method for determining an amount of an impurity in a composition sample comprising lomitapide or a pharmaceutically acceptable salt thereof, the method comprising:

determining an amount of a compound selected from:

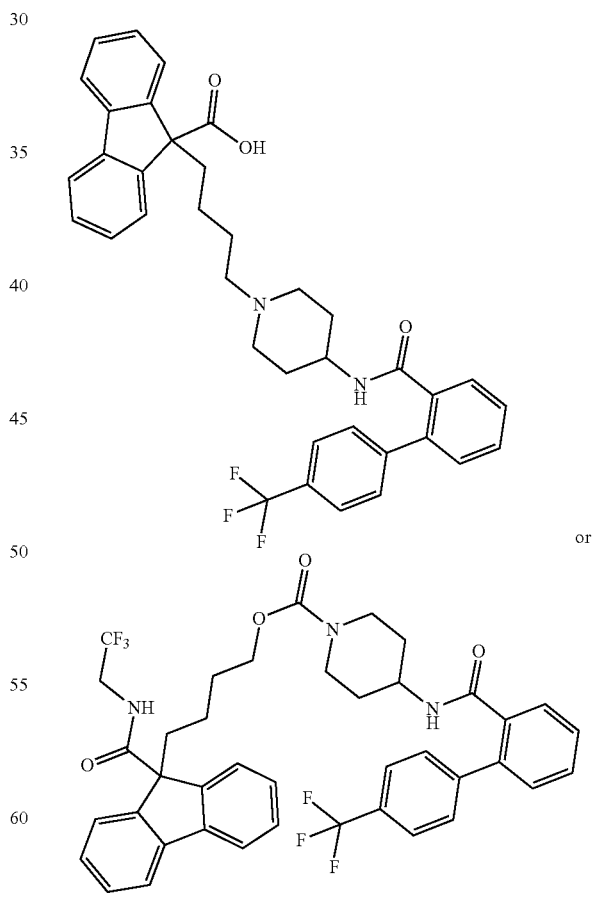

in the sample; and correlating the amount the compound in the sample with the amount of lomitapide in the sample.

REFERENCES

All publications and patents mentioned herein, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A lomitapide product having the following structure:

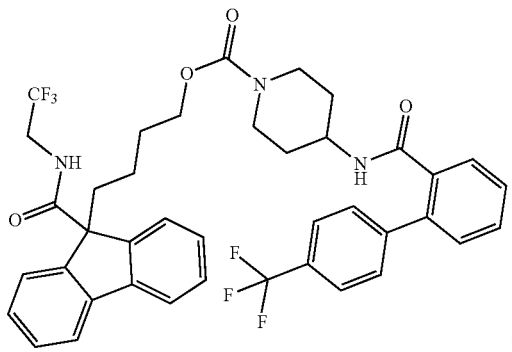 [SMILES: O=C(NC1CCN(C(=O)OCCCCC2(C(=O)NCC(F)(F)F)c3ccccc3-c3ccccc32)CC1)c1ccccc1-c1ccc(C(F)(F)F)cc1]

2. A lomitapide composition comprising: lomitapide or a pharmaceutically acceptable salt thereof the lomitapide product of claim 1; and
a pharmaceutically acceptable excipient.

3. A tablet comprising the lomitapide composition of claim 2.

4. The composition of claim 2, wherein the lomitapide product is present in an amount of less than about 0.5 weight percent.

5. The composition of claim 2, wherein the lomitapide product is present in an amount of less than about 0.1 weight percent after storage at 25° C. for 12 months.

6. A method for analyzing a lomitapide composition sample for the presence or amount of an impurity comprising:
providing a lomitapide composition sample;
using a spectral or toxicology analysis to determine the presence of a compound having the structure:

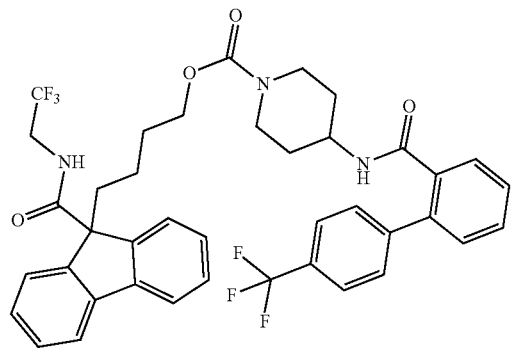

making a determination about the lomitapide composition sample based on a comparison of the compound and a reference standard for lomitapide or a pharmaceutically acceptable salt thereof; and determining the presence or amount of the compound thereby to analyze the lomitapide composition sample.

7. The method of claim 6, wherein the determination about the lomitapide composition sample is based on a comparison of a structural signal associated with of the compound and a reference standard for lomitapide or a pharmaceutically acceptable salt thereof.

8. The method of claim 7, wherein a level of the structural signature is calculated as the area under the curve or as the percent relative amount of each fraction present in the lomitapide composition sample.

9. The method of claim 7, wherein the structural signature is determined using high performance liquid chromatography (HPLC).

10. The method of claim 7, wherein the structural signature is determined using nuclear magnetic resonance (NMR) spectroscopy.

11. The method of claim 7, wherein the structural signature is determined using matrix-assisted laser desorption/ionization mass spectroscopy (MALDI-MS).

12. The method of claim 7, wherein the structural signature is determined using one or more of a fluorometric assay, an enzyme-linked immunosorbent assay (ELISA), a chromatogenic assay, and a colorimetric assay.

13. The method of claim 7, wherein the presence of the structural signature associated with the compound is determined to analyze the lomitapide composition sample.

14. The method of claim 6, wherein the determination about the lomitapide composition sample is based on a comparison of the molecular weight associated with of the compound and a reference standard for lomitapide or a pharmaceutically acceptable salt thereof.

15. The method of claim 14, wherein the molecular weight associated with the compound is determined to analyze the lomitapide composition sample.

16. A method for determining an amount of an impurity in a composition sample comprising lomitapide or a pharmaceutically acceptable salt thereof, the method comprising:

determining an amount of a compound having the structure:
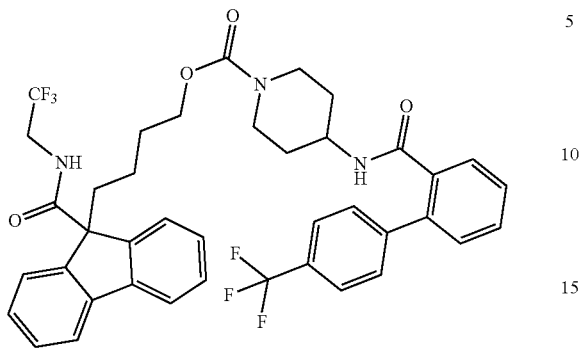
in the sample; and
correlating the amount the compound in the sample with the amount of lomitapide in the sample.
* * * * *